United States Patent
Drees et al.

(10) Patent No.: US 6,720,457 B2
(45) Date of Patent: Apr. 13, 2004

(54) PROCESS FOR THE HYDROFORMYLATION OF HIGHER OLEFINS USING COBALT COMPOUNDS AS CATALYST

(75) Inventors: Stefan Drees, Duelmen (DE); Bernhard Scholz, Marl (DE); Alfred Kaizik, Marl (DE); Walter Toetsch, Marl (DE); Wilfried Bueschken, Haltern (DE); Martin Trocha, Essen (DE)

(73) Assignee: Oxeno Olefinchemie GmbH, Marl (DE)

(*) Notice: Subject to any disclaimer, the term of this patent is extended or adjusted under 35 U.S.C. 154(b) by 0 days.

(21) Appl. No.: 10/200,752

(22) Filed: Jul. 24, 2002

(65) Prior Publication Data

US 2003/0032843 A1 Feb. 13, 2003

(30) Foreign Application Priority Data

Jul. 24, 2001 (DE) .......... 101 35 906

(51) Int. Cl.$^7$ .......... C07C 45/49
(52) U.S. Cl. .......... 568/429; 568/444; 568/451; 568/861; 568/862; 568/882
(58) Field of Search .......... 568/429, 444, 568/451, 861, 862, 882

(56) References Cited

U.S. PATENT DOCUMENTS

| | | | |
|---|---|---|---|
| 4,517,395 A | 5/1985 | Obenaus et al. | |
| 4,777,316 A | * 10/1988 | Harandi et al. | |
| 6,015,928 A | 1/2000 | Gubisch et al. | 568/882 |
| 6,184,424 B1 | 2/2001 | Bueschken et al. | |
| 6,239,318 B1 | 5/2001 | Schuler et al. | |
| 6,303,535 B1 | 10/2001 | Scholz et al. | |
| 6,331,657 B1 | 12/2001 | Kaizik et al. | |
| 6,403,836 B2 | 6/2002 | Kaizik et al. | |
| 6,407,295 B1 | 6/2002 | Kaizik et al. | |

FOREIGN PATENT DOCUMENTS

| | | |
|---|---|---|
| DE | 1 106 307 | 5/1961 |
| DE | 196 54 340 | 8/1998 |
| DE | 199 39 491 | 2/2001 |
| DE | 100 09 207 | 8/2001 |
| EP | 0 850 905 | 7/1998 |
| GB | 875565 | 8/1961 |
| WO | WO 92/13818 | 8/1992 |

OTHER PUBLICATIONS

Y. Chauvin, et al., Applied Homogeneous Catalysts with Organometallic Compounds, Aqueous–Phase Organometallic Catalysis, pp. 258–264, "Dimerization and Codimerization", 1996.

R. H. Friedlander, et al., Hydrocarbon Processing, pp. 31–33, "Make Plasticizer Olefins Via N–Butene Dimerization", Feb. 1986.

B. L. Haymore, et al., Annals New York Academy of Sciences, vol. 415, pp. 159–175, "Regioselectivity in Hydroformylation of Linear and Branched Octenes Using $HCo(CO)_4$", 1983.

J. Falbe, New Syntheses with Carbon Monoxide, pp. 94–123 and 164–165, "Hydroformylation of Particular Structures", 1980.

* cited by examiner

Primary Examiner—Johann Richter
Assistant Examiner—Sikarl A. Witherspoon
(74) Attorney, Agent, or Firm—Oblon, Spivak, McClelland, Maier & Neustadt, P.C.

(57) ABSTRACT

Olefins having from 5 to 24, in particular from 5 to 12, carbon atoms are hydroformylated by reacting an olefin or a mixture of olefins in the presence of an unmodified cobalt catalyst in a single-stage process in a reactor at a temperature of from 100° C. to 220° C. and a pressure of from 100 bar to 400 bar, to obtain an aldehyde, an alcohol or a mixture thereof. An aqueous bottom phase and an organic phase are present in the reactor, the aqueous bottom phase is mixed with the organic phase, and a concentration of the cobalt catalyst, calculated as metallic cobalt, in the aqueous bottom phase is in the range from 0.4 to 1.7% by mass based on the total weight of the aqueous bottom phase. A level of the aqueous bottom phase in the reactor is kept constant during steady-state operation.

20 Claims, No Drawings

PROCESS FOR THE HYDROFORMYLATION OF HIGHER OLEFINS USING COBALT COMPOUNDS AS CATALYST

BACKGROUND OF THE INVENTION

1. Field of the Invention

The invention relates to a process for the hydroformylation of higher olefins in the presence of an unmodified cobalt carbonyl complex by maintaining a aqueous bottom phase in the hydroformylation reactor.

2. Discussion of the Background

It is known that higher alcohols, in particular those having from 6 to 25 carbon atoms, can be prepared by catalytic hydroformylation (oxo process) of the olefins having one less carbon atom and subsequent catalytic hydrogenation of the aldehyde- and alcohol-containing reaction mixtures. They are used predominantly for the preparation of plasticizers and detergents. However, it is also possible to separate off aldehydes by distillation of the hydroformylation mixtures. These aldehydes can, for example, be utilized for preparing carboxylic acids.

The type of catalyst system and the optimum reaction conditions for the hydroformylation are dependent on the reactivity of the olefin used. The dependence of the reactivity of the olefin on this structure is described, for example, by J. Falbe, New Syntheses with Carbon Monoxide, Springer-Verlag, Berlin, Heidelberg, New York, 1980, page 95 ff. The differing reactivity of, in particular, the isomeric octenes is likewise known (B. L. Haymore, A. van Hasselt, R. Beck, Annals of the New York Acad. Sci., 415 (1983), pages 159–175).

Industrial olefin mixtures which are used as starting materials for the oxo process comprise olefin isomers having various structures and different degrees of branching, different positions of the double bond in the molecule and possibly also different numbers of carbon atoms. This applies particularly to olefin mixtures which have been formed by dimerization or trimerization or further oligomerization of $C_2$–$C_5$-olefins or other readily available higher olefins or by cooligomerization of the olefins mentioned. Examples of typical isomeric olefin mixtures which can be converted by means of rhodium-catalyzed or preferably cobalt-catalyzed hydroformylation into the corresponding aldehyde and alcohol mixtures are tripropenes and tetrapropenes and also dibutenes, tributenes and tetrabutenes.

If alcohols having a low degree of branching are wanted as hydroformylation product, the hydroformylation is advantageously carried out using unmodified cobalt catalysts. Compared to rhodium catalysts, cobalt catalysts give, starting from the same olefin mixture, higher yields of the particularly valuable straight-chain oxo products.

The hydroformylation of olefins using unmodified cobalt catalysts can, apart from the catalyst work-up, be carried out in one or more stages.

However, the known multistage processes for preparing oxo aldehydes in the presence of unmodified cobalt catalysts have a series of engineering disadvantages. Thus, the preparation of the cobalt catalyst required for the hydroformylation requires two technically complicated process steps: precarbonylation and catalyst extraction. Due to the mass transfer processes occurring in the two process steps: gas/liquid mass transfer in the precarbonylation and liquid/liquid mass transfer in the catalyst extraction, two separate pressure-rated apparatuses, for example, stirred vessels or packed columns, are necessary. The actual hydroformylation subsequently takes place in another separate pressure reactor.

The German patent application DE 196 54 340 describes a process in which precarbonylation, catalyst extraction and olefin hydroformylation are carried out in one reactor. Compared to the known multistate processes, this process has the advantages of a lower capital outlay and lower operating costs. However, it has the disadvantage that carrying out the single-stage process is quite difficult, since the substeps of the process, e.g. catalyst formation, extraction of the catalyst into the organic phase and hydroformylation, occurs simultaneously. An aqueous cobalt salt solution in which the catalyst is formed is present in the lower part of the reactor. The hydroformylation occurs mainly in the homogeneous organic phase. Water and cobalt compounds are continuously carried out from the reactor in the hydroformylation mixture leaving the reactor and the synthesis gas which is taken off, so that further quantities of cobalt compounds and water continually have to be introduced.

Although the single-stage process has been found to be useful in overall terms, fluctuations in conversion and selectivity occur during operation and continuous operation is disrupted by precipitation of cobalt compounds and/or metallic cobalt.

SUMMARY OF THE INVENTION

It is an object of the present invention to provide a single-stage process in which the above-mentioned difficulties during continuous operation are avoided and the target products are obtained in high yield and with high selectivity.

This and other objects have been achieved by the present invention the first embodiment which includes a process for the hydroformylation of an olefin, comprising:

reacting said olefin or a mixture of olefins in the presence of an unmodified cobalt catalyst in a single-stage process in a reactor at a temperature of from 100° C. to 220° C. and a pressure of from 100 bar to 400 bar, to obtain an aldehyde, an alcohol or a mixture thereof;

wherein an aqueous bottom phase and an organic phase are present in said reactor;

wherein the aqueous bottom phase is mixed with the organic phase;

wherein a concentration of said cobalt catalyst, calculated as metallic cobalt, in said aqueous bottom phase is in the range from 0.4 to 1.7% by mass based on a total weight of said aqueous bottom phase; and wherein a level of the aqueous bottom phase in said reactor is kept constant during steady-state operation.

DETAILED DESCRIPTION OF THE INVENTION

It has been found by the present inventors that a single-stage process for the hydroformylation of olefins which gives the corresponding aldehydes and/or alcohols in high yields can be operated advantageously if the aqueous bottom phase is mixed with the organic phase using suitable engineering measures. Further, the cobalt concentration (calculated as metallic cobalt) in the aqueous bottom phase should be set to 0.4 to 1.7% by mass and an aqueous bottom phase having a constant level should be maintained in the reactor during steady-state operation. The cobalt concentration includes all values and subvalues therebetween, especially including 0.5, 0.6, 0.7, 0.8, 0.9, 1.0, 1.1, 1.2, 1.3, 1.4, 1.5 and 1.6% by mass based on the total mass of the aqueous bottom phase.

The present invention accordingly provides a process for the hydroformylation of olefins having from 5 to 24 carbon atoms, in particular from 5 to 12 carbon atoms, preferably from 5 to 10 carbon atoms and particularly preferably 8 or 9 carbon atoms to form the corresponding aldehydes and/or alcohols having from 6 to 25 carbon atoms, in particular from 6 to 13 carbon atoms, preferably from 6 to 11 carbon atoms and particularly preferably 9 or 10 carbon atoms in the presence of an unmodified cobalt catalyst. An unmodified cobalt catalyst comprises at least cobalt and carbonyl groups and optionally at least one of hydrogen, an olefin group or an alkyl group. Preferably, the unmodified cobalt catalyst does not comprise a ligand comprising an element of group V of the periodic table. Particularly preferably, the unmodified cobalt catalyst does not comprise a complex builder. Most preferably, the unmodified cobalt catalyst does not comprise phophines, azines or phosphinites. The process is carried out as a single-stage process at temperatures of from 100° C. to 220° C., preferably from 120 to 160° C., and pressures of from 100 bar to 400 bar, preferably from 200 to 280 bar. An aqueous phase and an organic phase are present in the reactor. In addition, an aqueous bottom phase is maintained in the reactor, the aqueous bottom phase is mixed into the organic phase by means of an engineering measure, the concentration of cobalt compounds (calculated as metallic cobalt) in the aqueous phase is in the range from 0.4 to 1.7% by mass and the level of the bottom phase in the reactor is kept constant or virtually constant during steady-state operation. The reaction temperature includes all values and subvalues therebetween, especially including 110, 120, 130, 140, 150, 160, 170, 180, 190, 200 and 210° C. The reaction pressure includes all values and subvalues therebetween, especially including 120, 140, 160, 180, 200, 220, 240, 260, 280, 300, 320, 340, 360 and 380 bar.

The hydroformylation and the separation of the cobalt catalyst from the hydroformylation product can, for example, be carried out as described in German patent application DE 196 54 340 A1. This is a one-stage process in which the olefins are introduced into the reactor together with an aqueous cobalt salt solution and synthesis gas, particularly preferably using a mixing nozzle. The reactor is preferably a cascaded bubble column reactor. The output from the reactor is subsequently oxidized in the presence of an aqueous solution of carboxylic acids, especially formic acid. After phase separation, part of the aqueous phase in which the cobalt salts are present is returned to the one-stage process and the organic phase is further worked up to isolate the product (aldehyde) or hydrogenated to give the corresponding alcohols. The aqueous solution which is returned to the hydroformylation reactor contains virtually as much cobalt as is carried out with the hydroformylation mixture.

In the process of the invention, the level of the aqueous bottom phase in the hydroformylation reactor is kept constant or virtually constant. This means that, during steady-state operation (constant operating conditions), the phase boundary between the lower aqueous phase in which part of the organic phase is dispersed and the upper phase in which part of the aqueous phase is dispersed is established at a level whose height fluctuates by not more than ±5% around a mean. This mean height of the phase boundary can, in the process of the invention, be below or above or at the level of the exit orifice of the mixing nozzle through which the starting materials are introduced in the reactor. In an industrial embodiment, the phase boundary can be located, for example, from 0 to 1 m, in particular from 0 to 0.5 m, particularly preferably from 0 to 0.2 m, above or below the exit orifice of the mixing nozzle. The distance of the phase boundary to the exit orifice of the mixing nozzle includes all values and subvalues therebetween, especially including 0.1, 0.2, 0.3, 0.4, 0.5, 0.6, 0.7, 0.8 and 0.9 m.

It is important to keep the level of the phase boundary in the reactor constant, since otherwise fluctuations in the cobalt concentration in the aqueous phase are unavoidable, which could cause operating malfunctions. However, the absolute height of the phase boundary also has an influence on the reaction behavior. If the phase boundary is significantly above the mixing nozzle, the conversion is reduced because the ejector action of the mixing nozzle is no longer fully effective. A phase boundary which is too low leads to local temperature peaks, which can cause decomposition of the catalyst. The optimum height of the phase boundary in order to achieve a maximum yield and/or selectivity thus depends on the specific concentrations in the reactor, for example on the cobalt concentration in the aqueous phase, and on the other process parameters; the phase boundary therefore has to be matched in each case to the prevailing operating conditions.

The aqueous phase in the lower part of the reactor occupies 0.5 to 20%, preferably 1 to 10%, particularly preferably 1 to 5% by volume of the liquid contents of the reactor. The volume of the aqueous phase includes all values and subvalues therebetween, especially including 1, 2, 3, 4, 5, 6, 7, 8, 9, 10, 11, 12, 13, 14, 15, 16, 17, 18 and 19% by volume.

The amount of water carried from the reactor by the liquid hydroformylation mixture and by the excess synthesis gas is not a constant parameter. It depends on the operating parameters such as pressure, temperature, catalyst concentration and residence time, but especially on the composition of the hydroformylation mixture which partly determines the ability to dissolve water and thus the amount of water carried out. The alcohols formed by hydrogenation of the aldehydes, in particular, increase the solubility of water. Furthermore, the amount of water carried out changes during start-up or load changes.

In the process of the invention, fresh water and/or water which has been separated off at another point in the process, for example from the distillation of the organic phase of the organic hydroformylation product, can be fed in to maintain the level of the aqueous phase. The recirculated water streams can comprise starting materials, products and cobalt compounds.

The water can be introduced directly into the bottom of the reactor. Another possibility is to feed water in together with olefin and/or synthesis gas. Furthermore, water or an aqueous solution can be pumped into any circulation line for the aqueous reactor phase.

The discharge of cobalt compounds, too, is not constant over time, but depends on the operating parameters.

To set the cobalt concentration in the aqueous bottom phase in the reactor, cobalt compounds are metered in the process of the invention. The cobalt compounds are fed in as a solution, for example in product, starting material or water. Preference is given to using aqueous solutions of cobalt salts of carboxylic acids, for example cobalt formate or cobalt acetate. It is also possible to use solutions containing more than one cobalt compound. A particularly preferred cobalt salt solution is one which is obtained in the process itself during the removal of cobalt from the hydroformylation product. This solution, which further comprises formic acid, can be used directly or after increasing or reducing the formic acid content, for example as described in the German patent application DE 100 09 207.1.

In all cases, further cobalt and water are introduced in such amounts that the level of the aqueous bottom phase is kept effectively constant and the concentration of the cobalt compounds (calculated as metallic cobalt) in the aqueous bottom phase in the reactor is maintained in the range from 0.4 to 1.7% by mass, in particular in the range from 0.7 to 1.3% by mass. Lower cobalt concentrations are inadvisable, since the reaction rate then becomes too slow. Higher cobalt concentrations are likewise to be avoided, since they favor precipitation of cobalt compounds or metallic cobalt. This could result in blockages and adversely affect the function of instrumentation, which can lead to operating malfunctions. The cobalt concentration is monitored, advantageously by on-line analysis.

To obtain a high reaction rate, it is advantageous to mix the aqueous bottom phase with the organic phase and synthesis gas and also the aqueous phase. This intensive mixing avoids concentration gradients of the reactants. Furthermore, mixing of the aqueous bottom phase with the organic phase promotes transfer of the catalyst formed into the organic phase in which the hydroformylation mainly occurs.

The mixing of the reaction components (olefin, synthesis gas, aqueous cobalt salt solution) with themselves and/or the hydroformylation mixture and the mixing of the two liquid phases in the reactor can be carried out by means of appropriate devices.

Olefin, synthesis gas and aqueous cobalt salt solution can be introduced into the reactor separately, advantageously through nozzles. It is also possible for two components to be fed into the reactor together through one or more mixing nozzles and the third component to be fed in separately. However, it is particularly preferred to introduce all three components into the reactor together through one or more mixing nozzles.

The aqueous bottom phase can be circulated using a pump installed in a circulation line. Mixing of the aqueous phase and mixing of the aqueous phase with the organic phase and synthesis gas can also be achieved by part of the aqueous phase being taken from the reactor and fed into the mixing nozzle for the starting materials. This can be achieved by means of a pump. Another possibility is to allow part of the aqueous bottom phase to be sucked from the reactor into the stream flowing through the mixing nozzle.

The ejector action of mixing nozzles is influenced by the momentum of the exiting gas and the exiting liquid. High liquid velocities are from 3 to 300 m/s, in particular from 10 to 100 m/s, very particularly preferably from 15 to 70 m/s, at the point or points at which mixing-in occurs are advantageous. The liquid velocity includes all values and subvalues therebetween, especially including 20, 40, 60, 80, 100, 120, 140, 160, 180, 200, 220, 240, 260 and 280 m/s.

The starting materials for the process of the invention are olefins or mixtures of olefins having from 5 to 24 carbon atoms, in particular from 5 to 12 carbon atoms, preferably from 5 to 10 carbon atoms and particularly preferably 8 or 9 carbon atoms and terminal and/or internal C—C double bonds. Particularly preferred starting materials are mixtures of isomeric octenes and nonenes, i.e. oligomers of lower olefins such as n-butenes, isobutene or propene. Other starting materials which are likewise well suited are dimers of $C_5$-olefins. The oligomerization of butenes to form mixtures which consist essentially of $C_8$-olefins can in principle be carried out according to three process variants. Oligomerization over acid catalysts, for example zeolites or phosphoric acid on supports in industrial practice, has long been known. This gives isomer mixtures of branched olefins which are essentially dimethylhexenes (WO 92/13818). Another process which is likewise employed worldwide is oligomerization using soluble nickel complexes, known as the DIMERSOL process (B. Comils, W. A. Herrmann, Applied Homogeneous Catalysis with Organometallic Compounds; Vol. 1 & 2, pp 258–264, VCH, Weinheim, N.Y. 1996). The third process variant is oligomerization over fixed-bed nickel catalysts; this process is described in the literature as the OCTOL process (Hydrocarbon Process, Int. Ed. (1986) 65 (2. Sect. 1), pages 31–33).

The process of the present invention is preferably carried out using olefins or olefin mixtures which have been prepared by oligomerization over fixed-bed nickel catalysts.

The hydroformylation mixtures can be used for preparing aldehydes. However, the hydroformylation mixtures can also be hydrogenated to give the corresponding alcohols. An important application of the alcohols which can be prepared in this way is their use for preparing plasticizers, for example phthalic esters.

German patent application 10135906.3, filed Jul. 24, 2001, is incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A process for the hydroformylation of an olefin, comprising:

reacting said olefin or a mixture of olefins in the presence of an unmodified cobalt catalyst in a single-stage process in a reactor at a temperature ranging from 100° C. to 220° C. and a pressure ranging from 100 bar to 400 bar, to obtain an aldehyde, an alcohol or a mixture thereof;

wherein an aqueous bottom phase and an organic phase are present in said reactor;

wherein the aqueous bottom phase is mixed with the organic phase;

wherein the concentration of said cobalt catalyst, calculated as metallic cobalt, in said aqueous bottom phase is in the range from 0.4 to 1.7% by weight based on the total weight of said aqueous bottom phase; and wherein the level of the aqueous bottom phase in said reactor is kept constant during steady-state operation.

2. The process as claimed in claim 1, wherein the concentration of the cobalt catalyst in the aqueous bottom phase is in the range from 0.7 to 1.3% by weight.

3. The process as claimed in claim 1, wherein the aqueous bottom phase occupies from 0.5 to 20 vol. % of the liquid contents of the reactor.

4. The process as claimed in claim 3, wherein the aqueous bottom phase occupies from 1 to 10 vol. % of the liquid contents of the reactor.

5. The process as claimed in claim 1, wherein a phase boundary is present between the aqueous bottom phase and the organic phase which ranges in position from 0 to 1 m below or above the exit orifice of a mixing nozzle.

6. The process as claimed in claim 1, wherein the aqueous bottom phase is mixed with the organic phase.

7. The process as claimed in claim 1, wherein the aqueous phase is mixed with the organic phase because of the ejector action of a mixing nozzle.

8. The process as claimed in claim 7, wherein a liquid velocity at an outlet of the mixing nozzle ranges from 3 to 300 m/s.

9. The process as claimed in claim 8, wherein the liquid velocity at the outlet of the mixing nozzle ranges from 10 to 100 m/s.

10. The process as claimed in claim 1, wherein the aqueous bottom phase is mixed with the organic phase by means of a circulation pump.

11. The process as claimed in claim 1, wherein said olefin has from 5 to 12 carbon atoms.

12. The process as claimed in claim 11, wherein said olefin has from 5 to 10 carbon atoms.

13. The process as claimed in claim 12, wherein said olefin has 8 or 9 carbon atoms.

14. The process as claimed in claim 13, wherein said olefin comprises a $C_8$-olefin mixture obtained by oligomerization over a fixed-bed nickel catalyst.

15. A hydroformylation mixture obtained by the process according to claim 1.

16. The hydroformylation mixtures according to claim 15, comprising:

an aldehyde, an alcohol or a mixture thereof.

17. The process as claimed in claim 1, wherein said unmodified cobalt catalyst comprises cobalt and a carbonyl group.

18. The process as claimed in claim 17, wherein said cobalt catalyst further comprises hydrogen.

19. The process as claimed in claim 17, wherein said cobalt catalyst further comprises an olefin group or an alkyl group.

20. The process as claimed in claim 17, wherein said cobalt catalyst does not comprise a ligand having an element of Group V of the Periodic Table.

* * * * *